United States Patent
Wyler et al.

(10) Patent No.: US 8,197,503 B2
(45) Date of Patent: Jun. 12, 2012

(54) SIDE LOADING LANCING DEVICE

(75) Inventors: Jonathan M. Wyler, Boston, MA (US); Ray Adams Lathrop, Nashville, TN (US); John Andrew Trissel, Canton, GA (US); David Buenger, Roswell, GA (US)

(73) Assignee: Abbott Diabetes Care Inc., Alameda, CA (US)

( * ) Notice: Subject to any disclaimer, the term of this patent is extended or adjusted under 35 U.S.C. 154(b) by 594 days.

(21) Appl. No.: 12/192,458

(22) Filed: Aug. 15, 2008

(65) Prior Publication Data

US 2010/0042132 A1    Feb. 18, 2010

(51) Int. Cl.
*A61B 17/14*    (2006.01)

(52) U.S. Cl. ........................................ 606/182

(58) Field of Classification Search .................. 606/181, 606/182, 183; 604/136, 137, 138, 139; 600/583
See application file for complete search history.

(56) References Cited

U.S. PATENT DOCUMENTS

| 4,416,279 | A  |   | 11/1983 | Lindner et al. |            |
|-----------|----|---|---------|----------------|------------|
| 4,577,630 | A  |   | 3/1986  | Nitzsche et al.|            |
| 5,707,384 | A  | * | 1/1998  | Kim            | 606/181    |
| 6,616,616 | B2 |   | 9/2003  | Fritz et al.   |            |
| 2002/0077650 | A1 |   | 6/2002 | Schraga     |            |
| 2003/0109895 | A1 | * | 6/2003 | Taylor et al. | 606/181 |
| 2004/0098008 | A1 |   | 5/2004 | Taylor et al. |         |
| 2004/0254599 | A1 | * | 12/2004 | Lipoma et al. | 606/181 |
| 2005/0154410 | A1 |   | 7/2005 | Conway et al. |         |
| 2008/0077168 | A1 |   | 3/2008 | Nicholls et al. |       |
| 2008/0109024 | A1 |   | 5/2008 | Berkovitch et al. |     |

FOREIGN PATENT DOCUMENTS

| EP | 1917910 A2     | 5/2008  |
| JP | WO2008/041438  | 4/2008  |
| WO | WO 20051107595 | 11/2005 |
| WO | 2009022136 A1  | 2/2009  |
| WO | 2009022138 A1  | 2/2009  |

OTHER PUBLICATIONS

PCT International Search Report (Date of Mailing: Nov. 2, 2009); PCT/US2009/053654, filed Aug. 13, 2009.

* cited by examiner

*Primary Examiner* — Ryan Severson
*Assistant Examiner* — Jonathan W Miles
(74) *Attorney, Agent, or Firm* — Young Basile

(57) ABSTRACT

A lancing device including a rail having opposed side surfaces, a lancet that is receivable on the rail, and a firing mechanism configured to propel the lancet. The lancet has a sharp tip and a body configured to engage the opposed side surfaces of the rail.

19 Claims, 5 Drawing Sheets

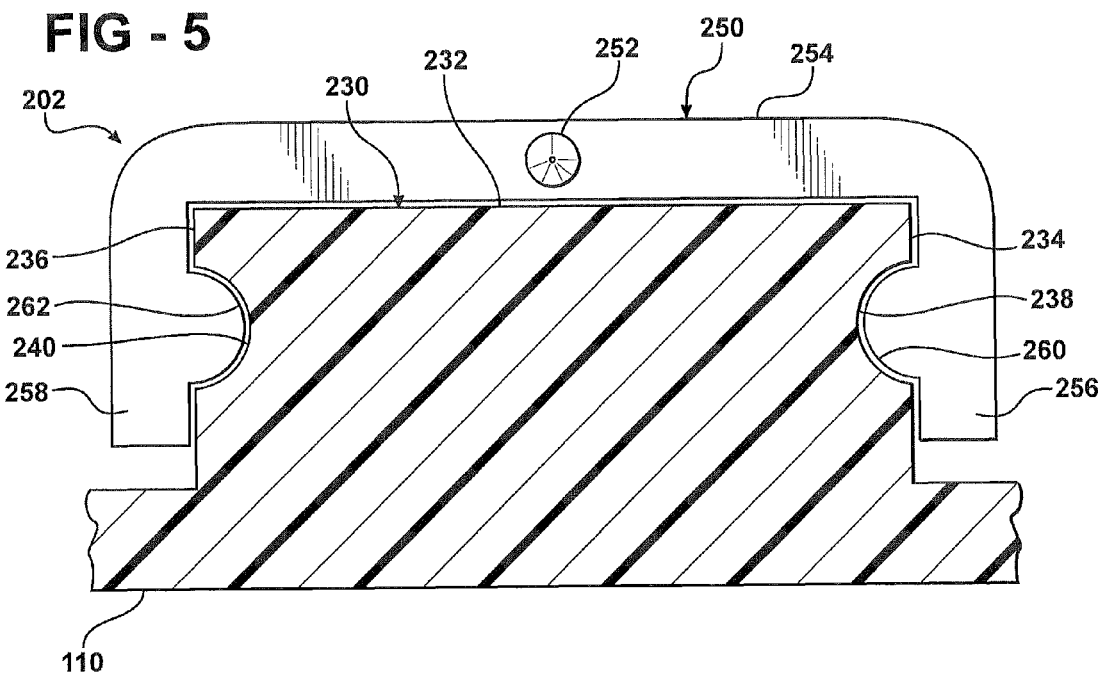
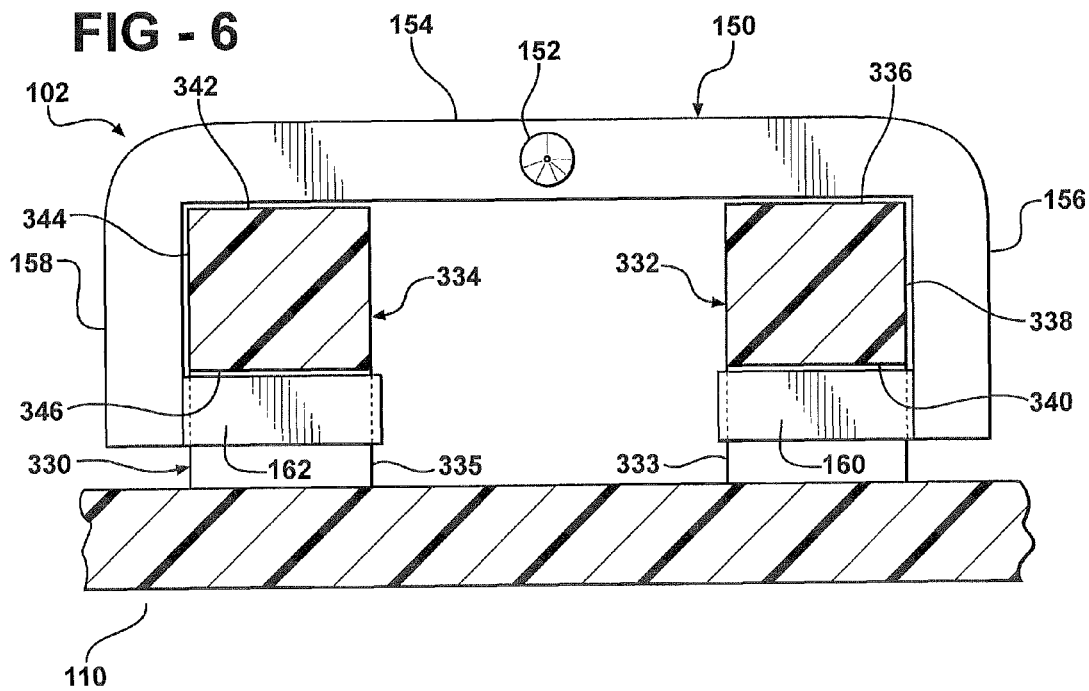

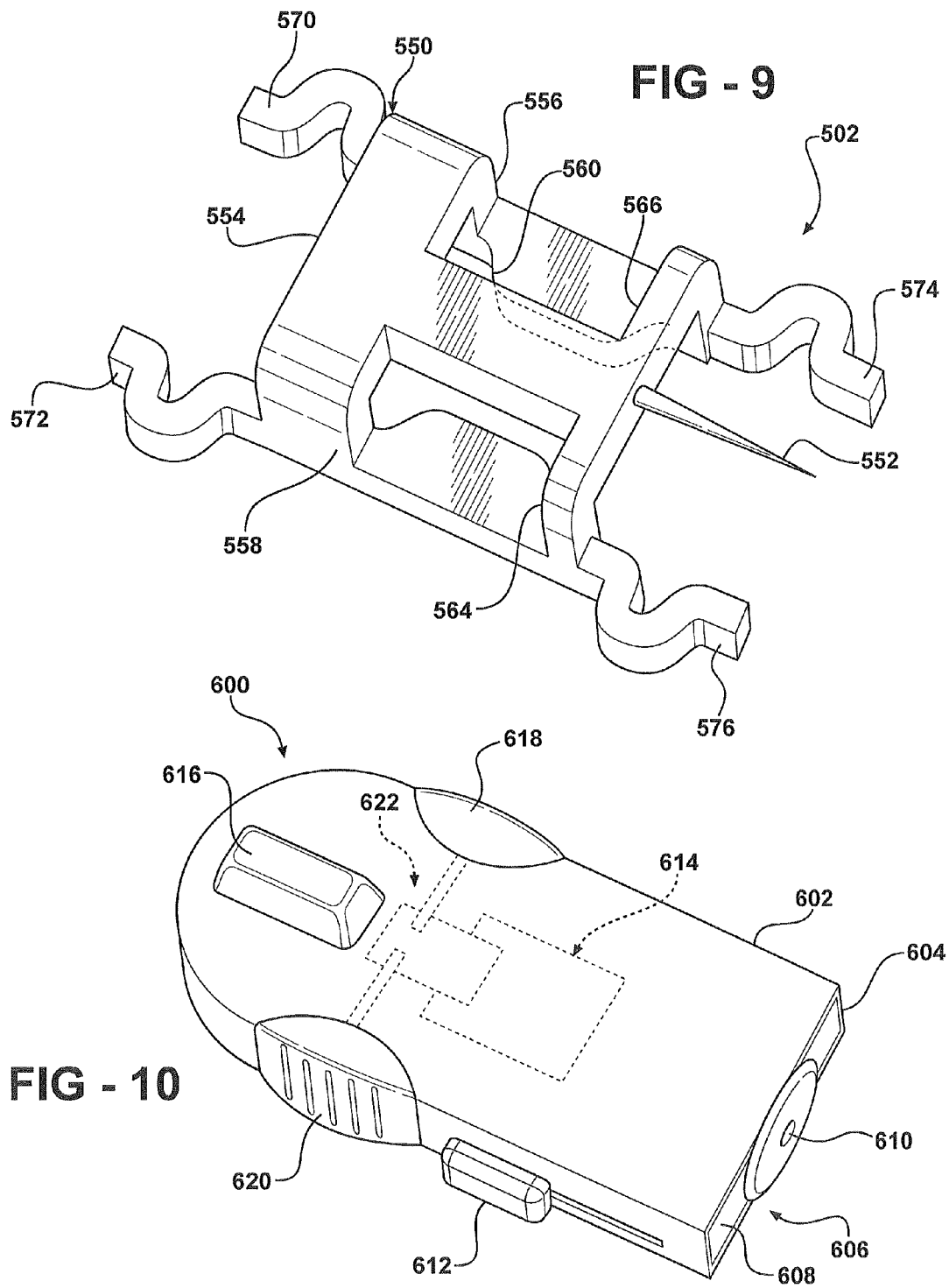

SIDE LOADING LANCING DEVICE

BACKGROUND

Lancing devices are typically handheld units that permit users to draw blood for testing and diagnostic purposes. These devices include a housing with a piercing aperture, a lancet that contains one or more needles, and a firing mechanism. The firing mechanism typically includes a spring or other biasing means which can be cocked either by insertion of the lancet or by pulling a cocking handle, for example. Once the lancing device is cocked, it is placed against the user's skin, often the fingertip. The user can then press a trigger to actuate the firing mechanism, which momentarily drives the sharp tip of the needle through the piercing aperture to puncture the user's skin and draw blood. When the lancing operation is complete, the user can press a second actuator to eject the lancet for removal and disposal. A consideration is the design of lancets and lancet devices is to minimize parts and thus minimize cost of production.

A consideration in the design of lancets is to minimize the discomfort experienced by users during the lancing process. To this end, some lancing devices include mechanisms to adjust the distance that the needle sharp protrudes through the piercing aperture, thus regulating the depth that the needle penetrates the user's skin. In some cases, these depth adjustment mechanisms include adjustable stops that limit the forward movement of the lancet during firing. In other cases, depth adjustment mechanisms adjust the tip of the lancing device to reduce or increase the distance that the needle sharp protrudes from the lancing device. One approach for depth adjustment is illustrated in U.S. Pat. No. 5,984,940. A lancet holder is moved axially within a lancing device housing to move the needle closer to or farther away from the piercing aperture, thus adjusting penetration depth.

Another consideration in the design of lancing devices is to avoid accidental needle pricks when inserting and removing lancets from the lancing device. To this end, lancets include safety features such as frangible tabs which cover the needle sharp prior to insertion in the lancing device. Once the lancet is inserted, the use can break off and remove the frangible tab. Some lancets also include sleeves coaxially mounted to the main body of the lancet. The sleeve can be positioned so that it protectively encloses the needle sharp. During the lancing operation, the main body of the lancet slides through the sleeve to expose the lancet sharp. After removal of the lancet, however, the sleeve can be locked in its protective position, reducing the likelihood that a person handling the use lancet will prick himself or herself.

It has also been proposed that a reference member be attached to the lancet itself. During incision, the lancet and the reference member are moved together toward the piercing aperture to effectively narrow the piercing aperture. After incision, the reference member and the lancet are retracted to leave the piercing aperture unobstructed. Prior to the lancet's insertion into the lancing device, the reference member can be adjusted relative to the lancet for purposes of regulating the penetration depth of the needle.

Another consideration in the design of lancing systems is the ease with which a lancet can be inserted into the lancing device. It is known that when a lancet is inserted into a lancing device, the force of the insertion can be used to cock the device. However, if the device is already cocked, and a lancet was to be inserted, there is some risk that the device would discharge during the insertion process and the user would be accidentally pricked. It is also known to provide a removable cap on the housing to permit insertion of the lancet. However, this requires an additional step in the process (namely, removing the cap).

Another consideration in the design of lancets is to minimize the handling of the lancet by the user during ejection of the lancet from the lancing device. To this end, it is known to provide ejection mechanisms that include a sliding member that engages the lancet to push it out of the lancing device. In such cases, it is helpful to restrain the lancet carrier from forward movement. Known mechanisms for achieving this use the sliding member to actuate a releasable connector to engage the lancet carrier and prevent its forward movement, as shown for example in U.S. Pat. No. 6,197,040. The releasable connector is biased towards the ejection slide and away from the lancet carrier and is configured so that when the lancet carrier is urged forward, a force vector is transmitted through the connector to the ejection slide. This means that the slide and the ejector rub against each other with a degree of force, causing friction that is discernable to the user.

SUMMARY

Lancing devices and methods of use are provided. In accordance with some embodiments of the invention, a lancing device includes a rail having opposed side surfaces, a lancet that is receivable on the rail, and a firing mechanism configured to propel the lancet. The lancet has a sharp tip and a body having a pair of runners that are configured to engage the opposed side surfaces of the rail. The firing mechanism could be configured to slide the lancet with respect to the rail.

The rail of the lancing device could include at least one upper surface and at least one lower surface, where the body of the lancet has a base portion configured to engage the upper surface of the rail and the runners are configured to engage the at least one lower surface of the rail. Alternatively, the rail of the lancing device could include opposed grooves, where the runners each have at least one projection adapted to extend into a respective groove of the opposed grooves of the rail. In some embodiments, the body of the lancet could is substantially c-shaped.

According to other embodiments of the invention, the lancing device includes a housing that has an opening, and a tray that is adapted to be received within the opening and slidably related to the housing for movement between an open position and a closed position, where the rail is disposed on the tray to facilitate installation and removal of the lancet.

According to some additional embodiments of the invention, the lancing device includes a housing, a first release button connected to the housing, and a second release button connected to the housing. Simultaneous operation of the first release button and the second release button actuates the firing mechanism. The lancing device could further include an interlock mechanism that prevents actuation of the firing mechanism unless both the first release button and the second release button are operated. Additionally, the first release button could be disposed on the housing opposite the second release button to allow the first and second buttons to be operated by a squeezing action.

According to further embodiments, the firing mechanism could include a firing spring to accelerate the lancet and a return spring to decelerate the lancet. In alternative embodiments, a firing spring could be connected to the lancet to accelerate the lancet, and a return spring could be connected to the lancet to decelerate the lancet.

BRIEF DESCRIPTION OF THE DRAWINGS

The description herein makes reference to the accompanying drawings wherein like reference numerals refer to like parts throughout the several views, and wherein:

FIG. 5 is a front cross section view of an alternative rail having an alternative lancet installed thereon;

FIG. 6 is a front cross section view of an alternative rail having an alternative lancet installed thereon;

FIG. 9 is a perspective view of the lancet of FIG. 8;

FIG. 10 is a perspective view of a lancing device in accordance with another embodiment of the invention.

DETAILED DESCRIPTION OF THE EMBODIMENTS

Figure 1:
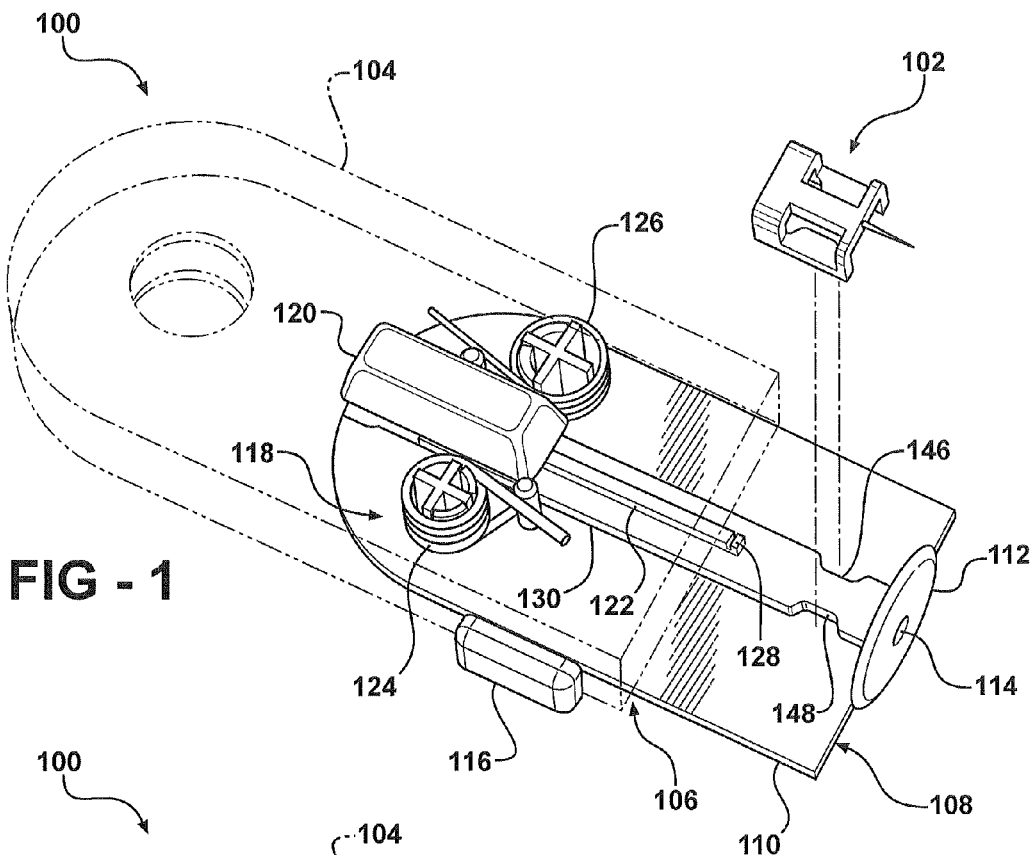
FIG. 1 is a perspective view of a lancing device in accordance with one embodiment of the invention prior to installation of a lancet on a rail of the lancing device.
Figure 2:
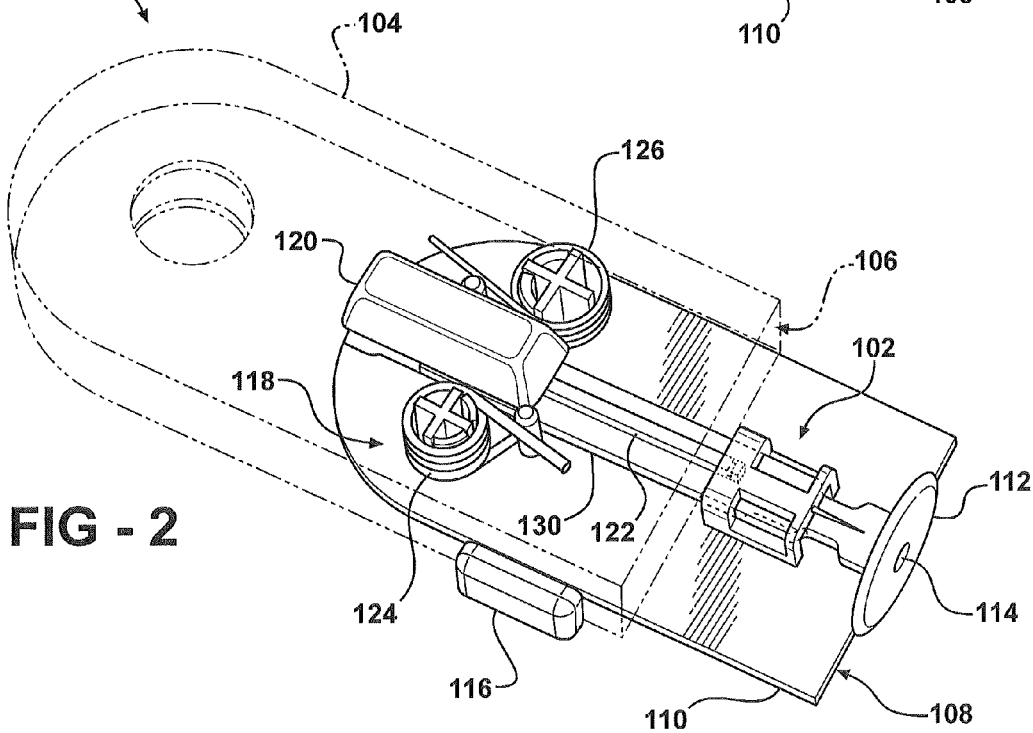
FIG. 2 is a perspective view of the lancing device of FIG. 1 having the lancet of FIG. 1 installed on the rail of the lancing device.

FIGS. 1-2 show a lancing device 100 and a lancet 102 in accordance with an embodiment of the invention. The lancing device 100 includes a housing 104 having an opening 106, and a tray 108 that is receivable within the opening 106 for movement between a closed position an open position.

The tray 108 includes a base portion 110 and an end wall 112 through which a piercing aperture 114 extends. The end wall 112 could extend substantially perpendicular to the base portion 110. Also, the end wall 112 could substantially occupy the opening 106 when the tray 108 is in the closed position. A thumb button 116 may be connected to the tray 108 and extend through the housing 104 to facilitate movement of the tray 108 between the open and closed positions.

A firing mechanism 118 is mounted on the tray 108, and an operating button 120 is operatively connected to the firing mechanism 118. Manipulation of the operating button 120 allows the user to move the firing mechanism 118 to a cocked position subsequently release the firing mechanism 118 to propel the lancet 102 using a firing rod 124 that is connectable to the lancet 102 and thereby perform a piercing operation.

The firing mechanism 118 could include a firing spring 124 that is exerts a biasing force on the firing rod 122 when the firing mechanism 118 is in the cocked position to propel the firing rod 122 and the lancet 102 when the firing mechanism 118 is released. The firing mechanism could further include a return spring 126 that counters the force exerted on the firing rod 122 by the firing spring 124 to decelerate the firing rod 122 and the lancet 102 during the piercing operation. Of course, a single spring could be utilized to perform both firing and return functions.

The lancing device includes a rail 130 on which the lancet 102 is received. The rail 130 extends from the firing mechanism 118 to the end wall 112 of the tray 110 to guide the lancet 102 toward the piercing aperture 114 during the piercing operation.

Figure 3:
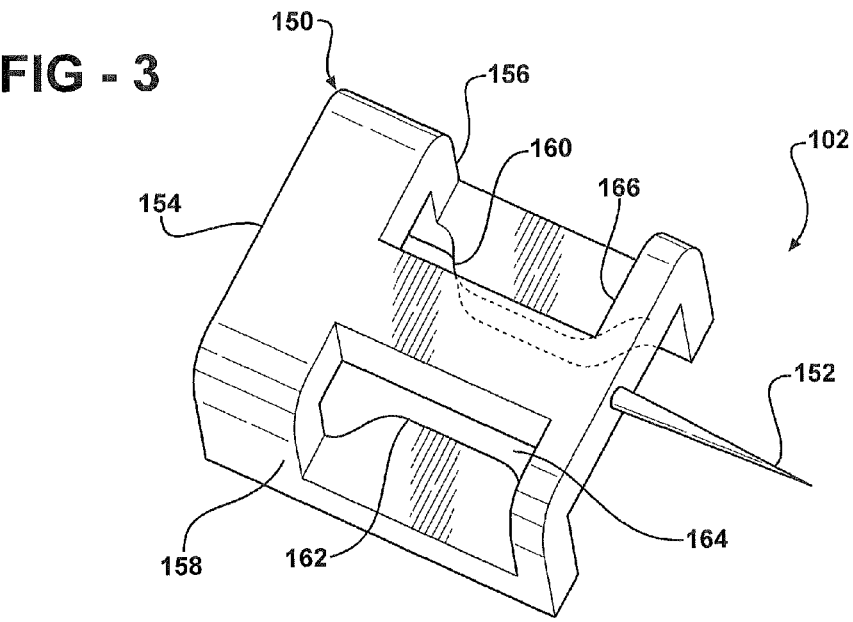
FIG. 3 is a perspective view of the lancet of FIG. 1.
Figure 4:
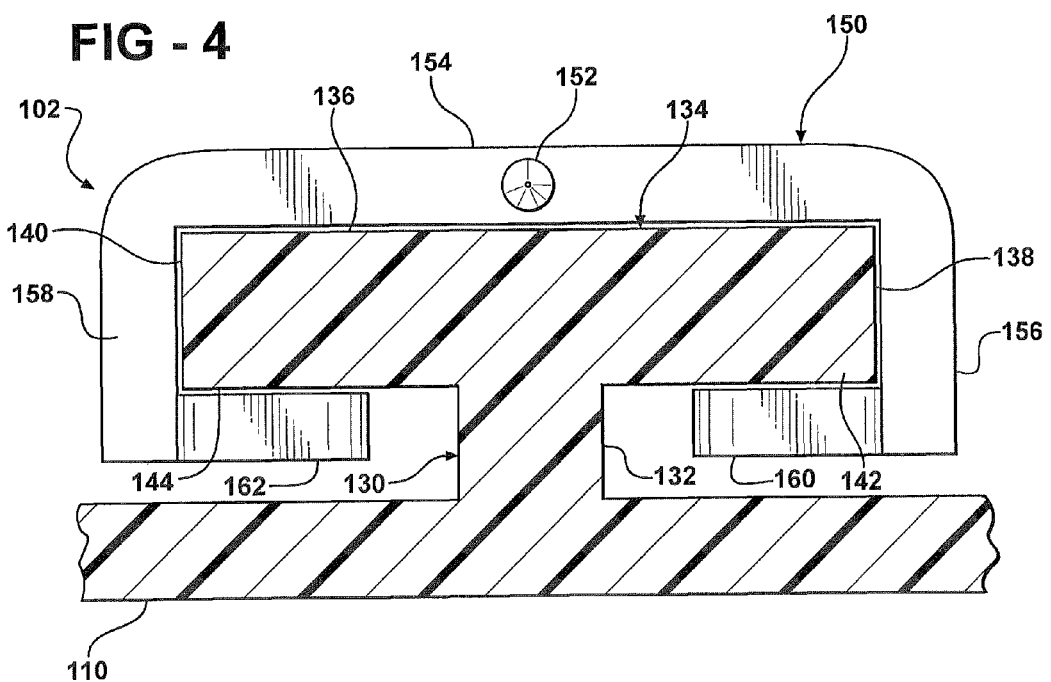
FIG. 4 is a front cross section view of the rail of FIG. 1 having the lancet of FIG. 1 installed thereon.

As shown in FIGS. 3-4, the lancet 102 has a body 150 and a sharp tip 152 that extends through the piercing aperture 114 during the piercing operation. The body 150 of the lancet 102 is substantially c-shaped, having a center portion 154, a first runner 156, and a second runner 158. As will be explained herein, the configuration of the body 150 of the lancet 102 allows the lancet 102 to be installed on the rail 130 transversely, as opposed to axially, reducing the possibility of inadvertent puncture of the user's skin by the sharp tip 152 during installation and removal of the lancet 102 with respect to the lancing device 100.

The first runner 156 and the second runner 158 of the body 150 of the lancet 102 are connected to the center portion 154 of the body 150 opposite one another, and each extends substantially perpendicular to the center portion 154. The first runner 156 and the second runner 158 can be substantially planar elements that are parallel to one another and spaced apart by the center portion 154. A first projection 160 is formed on the first runner 156 and a second projection 162 is formed on the second runner 158. The first projection 160 and the second projection 162 are extend perpendicularly inward from the first runner 156 and the second runner 158, respectively, and are spaced from the center portion 154.

A first window 164 and a second window 166 could be formed through the junctions of the center portion 154 of the body 150 of the lancet 102 and the first and second runners 156, 158 of the body 150, respectively, to allow the body 150 of the lancet 102 to be flexed. Provision of the windows 164, 166 allows the first and second projections 160, 162 to be resiliently moved with respect to one another and subsequently returned to their original positions.

The rail 130 may be substantially t-shaped, having a central leg 132 and a primary portion 134. The central leg 132 is connected to the base portion 110 of the tray, and spaces the primary portion 134 of the rail 130 from the base portion 110 of the tray.

The primary portion 134 of the rail 130 is substantially rectangular, and includes an upper surface 136, a first side surface 138, a second side surface 140, a first lower surface 142, and a second lower surface 144. The first side surface 138 extends perpendicularly downward from the upper surface 136, and the first lower surface 142 extends perpendicularly inward from the first side surface 138, terminating at the central leg 132. The second side surface 140 extends perpendicularly downward from the upper surface 136, and the second lower surface 144 extends perpendicularly inward from the second side surface 140, terminating at the central leg 132.

The lancet 102 is installed in the lancing device 100 by placing the lancet 102 on the rail 130 and engaging the lancet 102 with the firing mechanism 118. First, the tray 108 is moved to the open position, exposing the rail 130. Then, the lancet 102 is seated on the rail 130 by moving the lancet 102 transversely downward onto the rail by passing the first and second projections 160, 162 of the body 150 of the lancet 102 downward through a first notch 146 and a second notch 148 that are provided on the rail 130, as shown in FIG. 1. Next, the lancet 102 is engaged with a hook 128 that is provided on the firing rod 122 of the firing mechanism 118 to slide the lancet 102 with respect to the rail 130.

While the lancet 102 is on the rail 130, the body 150 of the lancet 102 engages the upper surface 136 of the rail 130 as well as the opposed first and second side surfaces 138, 140 of the rail 130 so that the motion of the lancet 102 is constrained by and guided along the rail 130. In particular, the center portion 154 of the body 150 engages the upper surface 136 of the rail 130, the first runner 156 of the body engages the first side surface 138 of the rail, and the second runner 158 of the body 150 engages the second side surface 140 of the rail 130. Thus, the rail 130 is at least partially disposed between the first runner 156 and the second runner 158.

To prevent the lancet 102 from disengaging the rail 130, the first projection 160 of the body 150 engages the first lower surface 142 of the rail 130 and the second projection 162 of the body 150 engages the second lower surface 144 of the rail 130. Thus, the rail 130 is at least partially disposed between the center portion 154 of the body 150 of the lancet and the first and second projections 160, 162, and the lancet 102 is restrained from moving upward and off of the rail 130 unless the projections 160, 162 of the lancet 102 are aligned with the notches 146, 148 of the rail 130.

According to an alternative embodiment, the lancing device 100 includes a rail 230 for use with a lancet 202, as shown in FIG. 5. The rail 230 includes a top surface 232, a first side surface 234 and a second side surface 236, where the first side surface 234 is opposite the second side surface 236. The first and second side surfaces 234, 236 extend perpendicularly downward from the top surface 232 of the rail 230 to the base portion 110 of the tray 108. A first groove 238 is formed in the first side surface 234 and a second groove 240 is formed in the second side surface 236. The grooves 238, 240 extend longitudinally along the rail 230, and may be provided in any desired shape, including, but not limited to, square, rectangular, semi-circular, arcuate, or triangular.

The lancet 202 includes a body 250 and a sharp tip 252. The lancet 202 is substantially u-shaped, having a center portion 254, a first runner 256, and a second runner 256. The first runner 256 and the second runner 256 are spaced from each other by the center portion 254 for engagement with the first side surface 234 and the second side surface 236 of the rail 230, respectively. The first runner 256 has a first projection 260 formed thereon and the second runner 258 has a second projection 262 formed thereon. The first projection 260 and the second projection 262 extend inward from the first runner 256 and the second runner 256, respectively. The first projection 260 and the second projection 262 are configured to be received in the first groove 238 and the second groove 240 of the rail 230, respectively, to retain the lancet 202 on the rail 230.

According to another alternative embodiment, the lancing device 100 includes a rail 330, as shown in FIG. 6, for use with the lancet 102. The rail 330 includes a first rail portion 332 and a second rail portion 334, where the first and second rail portions 332, 334 are formed separately, are spaced from one another, and extend substantially parallel to one another.

The first rail portion 332 includes a first upper surface 336, a first outer surface 338 and a first lower surface 340. The second rail portion 334 includes a second upper surface 342, a second outer surface 344 and a second lower surface 346. The first outer surface 338 and the second outer surface 344 serve as opposed outer surfaces of the rail 330. The first rail portion 332 includes legs 333 at its terminal ends to support and space that first rail portion 332 with respect to the base portion 110 of the tray 108. Likewise, the second rail portion 334 includes legs 335 at its terminal ends to support and space that second rail portion 334 with respect to the base portion 10 of the tray 108. The lancet 102 relates to the rail 330 as described in connection with the rail 130.

Figure 7:
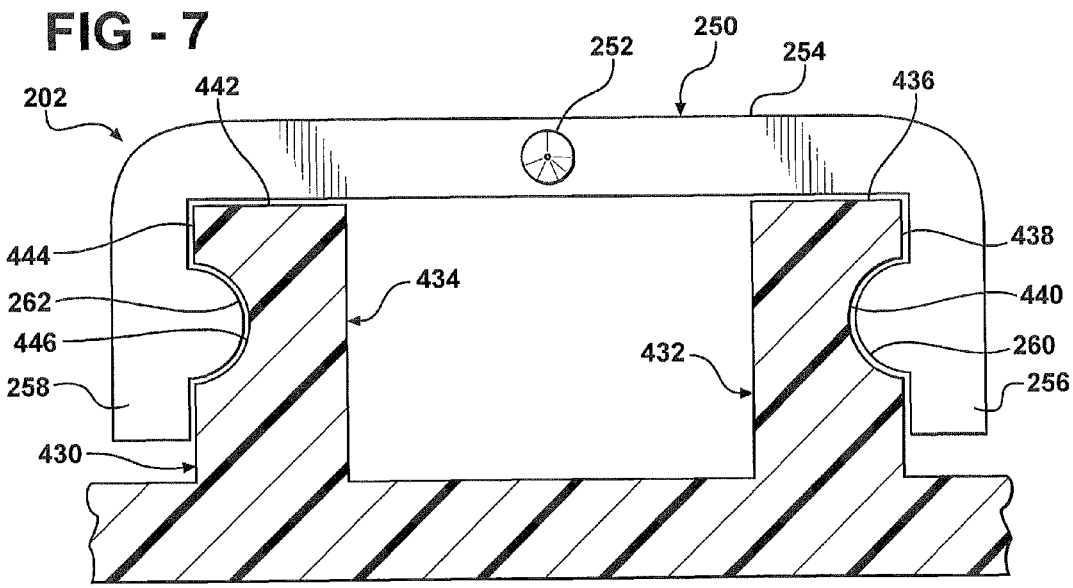
FIG. 7 is a front cross section view of an alternative rail having an alternative lancet installed thereon.

According to another alternative embodiment, the lancing device 100 includes a rail 430, as shown in FIG. 7, for use with the lancet 202. The rail 430 includes a first rail portion 432 and a second rail portion 434, where the first and second rail portions 432, 434 are formed separately, are spaced from one another, and extend substantially parallel to one another.

The first rail portion 432 includes a first upper surface 436, a first outer surface 438 and a first groove 440. The second rail portion 434 includes a second upper surface 442, a second outer surface 444 and a second groove 446. The first outer surface 438 of the first rail portion 432 and the second outer surface 444 of the second rail portion 434 serve as opposed outer surfaces of the rail 430. The first groove 440 is formed in the first side surface 438 of the first rail portion 432. The second groove 440 is formed in the second side surface 444 of the second rail portion 434. The grooves 440, 446 extend longitudinally along the rail 430, and may be provided in any desired shape, including, but not limited to, square, rectangular, semi-circular, arcuate, or triangular. The lancet 202 relates to the rail 430 as described in connection with the rail 230.

Figure 8:
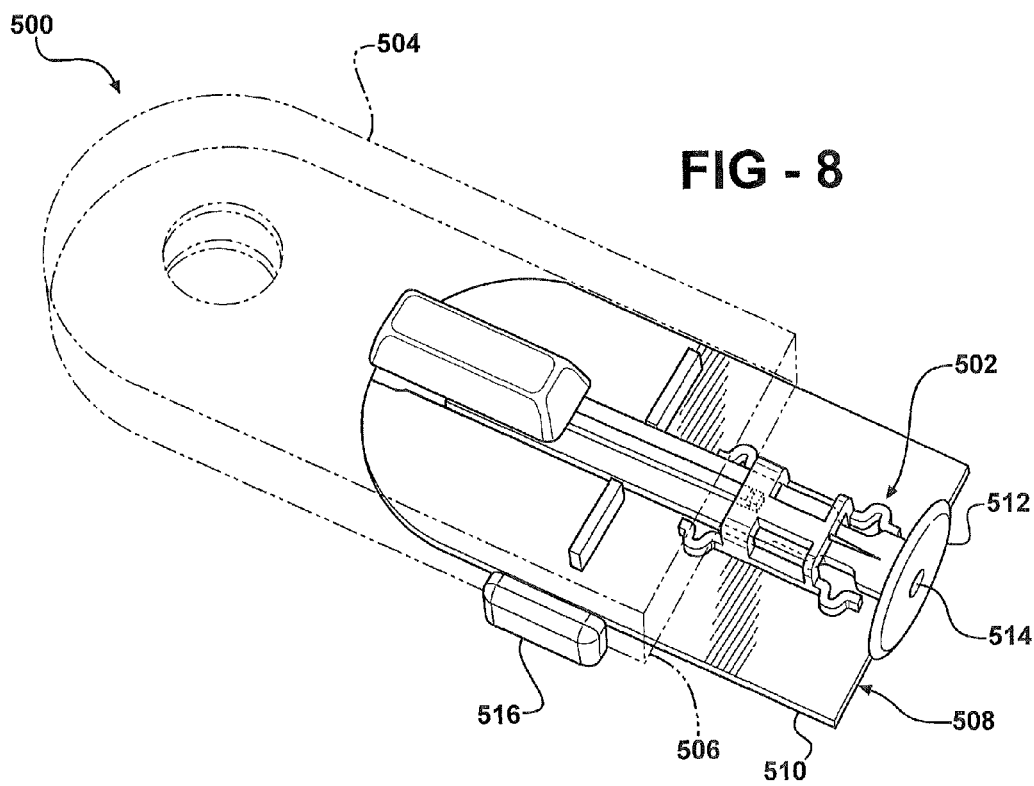
FIG. 8 is a perspective view of a lancing device having a lancet installed thereon in accordance with another embodiment of the invention.

FIG. 8 shows a lancing device 500 for use with an lancet 502 in accordance with another embodiment of the invention. The lancing device 500 includes a housing 504 having an opening 506, and a tray 508 that is receivable within the opening 506 for movement between a closed position an open position. The tray 508 includes a base portion 510, an end wall 512, a piercing aperture 514, and a thumb button 516, as described in connection with corresponding elements of the lancing device 100.

A firing mechanism 518 is mounted on the tray 508, and an operating button 520 is operatively connected to the firing mechanism 518, and a rail 530 extends from the firing mechanism 518 to the end wall 512 of the tray 510 to guide the lancet 502 toward the piercing aperture 514 during the piercing operation. However, the firing mechanism 518 lacks on-board biasing elements, which are instead provided on a lancet 502 that is provided for use with the lancing device 500.

As shown in FIG. 9, the lancet 502 has a body 550 and a sharp tip 552 that extends through the piercing aperture 514 during the piercing operation. The lancet 502 is substantially c-shaped, having a center portion 554, a first runner 556, a second runner 558, a first projection 560, a second projection 562, a first window 564 and a second window 566, as described in connection with corresponding elements of the lancet 102.

The lancet 502 includes a first firing spring 570, a second firing spring 572, a first return spring 574 and a second return spring 576, all of which could be formed integrally with the body 550 of the lancet 502. The first firing spring 570 extends rearward from the first runner 556. The second firing spring 572 extends rearward from the second runner 558. The first return spring 574 extends rearward from the first runner 556. The second return spring 576 extends rearward from the second runner 558. Each of the springs 570, 572, 574, 576 may be fabricated from plastic, as a slender member having a reverse curvature to provide sufficient resiliency to allow biasing of the lancet 502 sufficient to perform the firing and return functions during the piercing operation.

During the piercing operation, movement of the firing mechanism 518 to the cocked position engages the firing springs 570, 572 of the lancet 502 with a pair of wall members 522 that are provided on the tray 108 to facilitate compression of the firing springs 570, 572 to provide acceleration of the lancet 502 when the firing mechanism 518 is released. After release of the firing mechanism 518, the return springs 574, 576 engage the end wall 512 of the tray 508 to decelerate the lancet 502.

According to another embodiment of the invention, the lancing devices of the preceding embodiments may be provided with a squeeze-to-fire trigger, as will be explained in connection with a lancing device 600, as seen in FIG. 10. The lancing device 600 includes a housing 602, a tray 604 that is received in an opening in the housing 606. The tray 604 has an end wall 608 through which a piercing aperture 610 is formed. A thumb button 612 can be provided to facilitate movement of the tray 604 between open and closed positions.

The lancing device 600 includes a firing mechanism 614, which is substantially as described in connection with the corresponding elements of the lancing device 100. However, the lancing device 600 includes a cocking button 616 to move the firing mechanism 614 to the cocked position, and first and second release buttons 618, 620 to release the firing mechanism to perform the piercing operation.

The first release button 618 and the second release button 620 are connected to opposite sides of the housing with respect to one another to allow the first and second release buttons 618, 620 to be operated using by a squeezing action, wherein simultaneous operation of the first release button 618 and the second release button 620 is operative to release the firing mechanism 614. Furthermore, the first release button 618 and the second release button 620 can be connected to the firing mechanism 614 by a mechanical interlock 622. The mechanical interlock 622 prevents actuation of the firing mechanism 614 unless both the first release button 618 and the second release button 620 are operated simultaneously.

All other aspects of the construction and operation of the lancing device 600 are as described in connection with the lancing device 100.

The above-mentioned embodiments have been described in order to allow easy understanding of the present invention. The invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A lancing device comprising:
 a housing;
 a planar member having a longitudinal axis;
 a rail base supported by the planar member along the longitudinal axis;
 a rail extending along the rail base and configured to transversely receive a lancet over the rail opposite the planar member;
 a lancet configured to straddle the rail, the lancet having a sharp tip and a body; an end wall with a skin engaging surface and a piercing aperture, the end wall positioned at one end of the rail to slidably move with the rail and planar member in relation to the housing; and
 a firing mechanism configured to propel the lancet along the rail.

2. The lancing device of claim 1, wherein the rail extends transversely beyond the rail base, and the body of the lancet is configured to span the rail.

3. The lancing device of claim 2, wherein a groove if formed between the rail and the planar member on each side of the rail base; and lancet further comprising runners each having at least one projection adapted to extend into a respective groove.

4. The lancing device of claim 1, further comprising:
 the housing having an open end, the planar member being adapted to be received within the open end and slidably related to the housing for movement between an open position and a closed position, wherein the rail is exposed on the planar member to facilitate installation and removal of the lancet when the planar member is in the open position.

5. The lancing device of claim 4, wherein the end wall is configured to substantially occupy the open end when the planar member is in the closed position.

6. The lancing device of claim 5, wherein the rail extends between the firing mechanism and the end wall.

7. The lancing device of claim 1, further comprising:
 a housing;
 a first release button connected to the housing; and
 a second release button connected to the housing, wherein simultaneous operation of the first release button and the second release button actuates the firing mechanism.

8. The lancing device of claim 7, wherein the first release button disposed on the housing opposite the second release button to allow the first and second buttons to be operated by a squeezing action.

9. The lancing device of claim 1, further comprising:
 an interlock mechanism that prevents actuation of the firing mechanism unless both the first release button and the second release button are operated.

10. The lancing device of claim 1, wherein the firing mechanism includes a firing spring to move the lancet in a first direction along the rail and a return spring to move the lancet in a second direction along the rail.

11. The lancing device of claim 1, further comprising:
 a firing spring connected to the lancet to accelerate the lancet; and
 a return spring connected to the lancet to decelerate the lancet.

12. A lancing device, comprising:
 a housing having an open end;
 a rail slidably disposed within the housing;
 an end wall with a skin engaging surface and a piercing aperture, an end wall positioned at one end of the rail to slidably move with the rail in relation to the housing;
 a lancet having a body and a sharp tip, the lancet receivable on the rail such that the sharp tip extends toward an end wall, the body of the lancet being U-shaped with a base portion that spans a top surface of the rail and two side portions; and
 a firing mechanism configured to propel the lancet along the rail.

13. The lancing device of claim 12, wherein the side portions of the lancet each have a runner with at least one projection configured to retain the lancet on the rail.

14. The lancing device of claim 12, wherein the rail is configured to slidably relate to the housing for movement between an open position and a closed position, wherein the open position facilitates installation and removal of the lancet on the rail.

15. The lancing device of claim 12, further comprising:
 a first release button connected to the housing; and
 a second release button connected to the housing, wherein simultaneous operation of the first release button and the second release button actuates the firing mechanism.

16. The lancing device of claim 15, further comprising:
 an interlock mechanism that prevents actuation of the firing mechanism unless both the first release button and the second release button are operated.

17. The lancing device of claim 15, wherein the first release button is disposed on the housing opposite the second release button to allow the first and second buttons to be operated by a squeezing action.

18. A lancing device, comprising:
 a housing having an opening;
 a tray that is adapted to be received within the opening and slidably related to the housing for movement between an open position and a closed position;
 a rail longitudinally disposed on the tray and having opposing notches, the rail having an end wall with a skin engaging surface and a piercing aperture positioned at one end of the rail to slidably move with the rail in relation to the housing;
 a lancet having a base portion that spans a top surface of the rail and, a pair of runners that extend substantially parallel to the base and are configured to slide over the rail via the notches to engage the rail; and
 a firing mechanism configured to propel the lancet along the rail.

19. The lancing device of claim 18, further comprising:
 a first release button connected to the housing; and
 a second release button connected to the housing, the second release button disposed on the housing opposite the first release button to allow the first and second buttons to be operated by a squeezing action, wherein simultaneous operation of the first release button and the second release button actuates the firing mechanism.

* * * * *